United States Patent
Bogert et al.

Patent Number: 5,882,337
Date of Patent: Mar. 16, 1999

[54] TIP PROTECTION DEVICE

[75] Inventors: David L. Bogert, Plainville, Conn.; Thomas K. Sutton, Carrollton; Herbert Brown, Colleyville, both of Tex.

[73] Assignee: Johnson & Johnson Medical, Inc., Arlington, Tex.

[21] Appl. No.: 482,588

[22] Filed: Jun. 7, 1995

[51] Int. Cl.⁶ .................................................. A61M 5/00
[52] U.S. Cl. .......................................... 604/110; 604/198
[58] Field of Search ..................... 604/110, 192, 604/198, 263

[56] References Cited

U.S. PATENT DOCUMENTS

| | | |
|---|---|---|
| 4,117,809 | 10/1978 | Moorehead . |
| 4,332,323 | 6/1982 | Reenstierna ............................. 604/110 |
| 4,373,526 | 2/1983 | Kling ................................. 604/198 X |
| 4,762,516 | 8/1988 | Luther et al. . |
| 4,790,828 | 12/1988 | Dombrowski et al. . |
| 4,804,371 | 2/1989 | Vaillancourt . |
| 4,826,490 | 5/1989 | Byrne et al. . |
| 4,832,696 | 5/1989 | Luther et al. . |
| 4,834,718 | 5/1989 | McDonald . |
| 4,917,669 | 4/1990 | Bonaldo . |
| 4,931,048 | 6/1990 | Lopez . |
| 4,944,725 | 7/1990 | McDonald . |
| 4,950,252 | 8/1990 | Luther et al. . |
| 4,952,207 | 8/1990 | Lemieux . |
| 4,964,854 | 10/1990 | Luther . |
| 4,978,344 | 12/1990 | Dombrowski et al. . |
| 4,994,041 | 2/1991 | Dombrowski et al. . |
| 5,007,901 | 4/1991 | Shields . |
| 5,084,023 | 1/1992 | Lemieux . |
| 5,084,030 | 1/1992 | Byrne et al. . |
| 5,127,905 | 7/1992 | Lemieux . |
| 5,205,829 | 4/1993 | Lituchy . |
| 5,215,528 | 6/1993 | Purdy et al. . |
| 5,312,371 | 5/1994 | Dombrowski et al. . |
| 5,322,517 | 6/1994 | Sircom et al. ......................... 604/198 |
| 5,342,310 | 8/1994 | Ueyama et al. ....................... 604/110 |
| 5,478,313 | 12/1995 | White ................................... 604/192 |
| 5,531,704 | 7/1996 | Knotek ................................. 604/263 |
| 5,538,508 | 7/1996 | Steyn ................................... 604/192 |
| 5,549,570 | 8/1996 | Rogalsky ............................. 604/198 |
| 5,558,651 | 9/1996 | Crawford et al. .................... 604/110 |
| 5,562,624 | 10/1996 | Righi et al. ......................... 604/110 |

Primary Examiner—Ronald Stright, Jr.
Attorney, Agent, or Firm—Joseph F. Shirtz

[57] ABSTRACT

A safety cover, which securably and reliably prevents the readvancement of the tip of a cannula once it has been retracted thereinto, is designed having an elongate body which includes an axial channel having elements which displace and block linear passage of the cannula once it has been retracted. In a first embodiment the displacing elements are inwardly and rearwardly extending bristles which provide for unidirectional motion of the cannula relative to the safety cover, thereby locking the cannula once it has been retracted. In a second embodiment, the displacing element is the axial channel itself which has a curvate bias and distorts into a non-linear path once the cannula is retracted. In a third embodiment, the displacing element is a spring plate which, when compressed permits the cannula to pass through, but once the cannula has been retracted, expands to prevent the tip from being readvanced.

5 Claims, 7 Drawing Sheets

TIP PROTECTION DEVICE

BACKGROUND OF THE INVENTION

1. Field of the Invention

The present invention relates generally to stick prevention apparatus for protecting medical personnel from injury. More particularly, the present invention relates to tip covering elements having internal conformations which prevent a retracted needle from reemerging therethrough.

2. Description of Prior Art

Medical care of individuals in hospitals, clinics, and other health care facilities often includes the taking of blood samples, intravenous supplying of medication, and the introduction or removal of other fluids via cannulae, needles, or syringes. The present medical environment, in which there exist diseases, for example Acquired Immune Deficiency Syndrome, AIDS, for which there are no cures, and which are transmitted via blood to blood contact, has raised concerns relating to the potential for contaminated "needle sticks".

A wide variety of devices have been provided in the prior art for prevention against accidental contaminated "needle sticks". For example, U.S. Pat. No. 5,215,528 to Purdy et al. (hereinafter Purdy) teaches an assembly for introducing a catheter into a blood vessel, wherein there is provided a tip cover which includes an elastically deforming L-shaped. In an initial disposition, the L-shaped member is positioned in a deformed state with the cannula inserted fully through the cover. Once the cannula is retracted, however, the L-shaped member springs into a position to prevent reemergence of the needle. Manual repositioning of the L-shaped member is necessary to permit the cannula reemerge from the cover.

U.S. Pat. No. 5,127,905 to Lemieux teaches a protection cap, which is similar to the device disclosed by Purdy, as described above. In the Lemieux device an externally mounted rotating L-shaped lever is disposed along the axis of the cover, manual actuation of which by a user once the cannula is retracted prevents the cannula from re-emerging from the cover. Manual retraction of the external L-shaped lever from the path of the cannula permits the cannula to reemerge.

U.S. Pat. No. 4,826,490 to Byrne et al. (hereinafter Byrne) teaches a safety cover and syringe assembly wherein an external cylindrical sleeve, through which the cannula extends, is slidably mounted to a track on the external surface of the syringe. Sliding the external cylindrical sleeve relative to the cannula and the syringe, such that the cannula is fully retracted into the sleeve, causes a locking mechanism to engage between the syringe and the sleeve so that the cannula may not be advanced out of the sleeve without disengagement of the locking elements by a user.

A device, which is similar to the one disclosed in the Byrne reference, is U.S. Pat. No. 4,952,207 which is also to Lemieux. This reference teaches a safety cover for use with a cannula which has a radial notch along the shaft, near the tip. The internal structure of the cover includes a tab which engages the cannula in the notch once the cannula has been retracted. Rotation of the cannula, or the safety cover locks the cannula in position and prevents its reemergence.

As above, however, the Lemieux prevention means may be compromised by intentional, or random, manipulation of the device. While each device includes functional means for preventing "needle sticks" by interfering with the exposure of a cannula once it is retracted into a cover, it is of considerable concern for users of such devices that, if a means for disengaging the retaining element is provided, random forces may expose the contaminated cannula, thus presenting a danger to medical personnel. This concern is especially applicable to the variety of "needle stick" prevention devices which include externally mounted prevention means.

It is, therefore, a principal object of the present invention to provide a needle cover which includes an element or elements which prevent exposure of a contaminated cannula.

It is further an object of the present invention to provide a needle cover which cannot be compromised, whereby the cannula may reemerge therethrough, by application of random environmental forces, or by unintentional manipulation of the device.

It is further an object of the present invention to provide a needle cover which is more reliable in its safety aspects.

Other objects and advantages of the invention will be more fully apparent from the ensuing disclosure and appended claims.

SUMMARY OF THE INVENTION

The present invention is directed to a needle cover which includes an axial channel and an interior chamber, through which a cannula may extend. Along this axial channel and/or in the interior chamber, there is provided means for permitting unidirectional translation of a cannula. In an initial disposition, the cannula is fully inserted through the safety cover, with the cannula extending through the axial channel. After the cannula has been used and has become contaminated, the cannula is retracted (or the cover is advanced along the shaft of the cannula) such that the tip is fully within the cover. Once freed from the influence of the cannula, the means for permitting only unidirectional movement are engaged to prevent the cannula from reemerging from the cover.

A variety of embodiments of the present invention are contemplated, including reverse angled bristles, a notched (or ribbed) and curved internal channel, and interlocking spring elements. More specifically, in a first embodiment, a cylindrical safety cover comprises an axial through hole which extends along the elongate axis thereof. The axial through hole includes a forward portion, the surface of which comprises a plurality of reverse angled semi-flexible bristle members which permit the cannula to translate back into the cover. Once the cannula is retracted, however, the bristles block the axial channel and the forward translation of the cannula is prevented.

In a second embodiment, the axial channel is provided with a slight curvature, and the surface of the channel is ribbed. The cover itself is constructed of a semi-flexible and quasi-elastomeric material such that, in an initial disposition, the cannula may be inserted fully through the axial channel. After use, the cannula is retracted along the axial channel until the tip of the cannula is fully within the channel. Without the linear influence of the cannula shaft to prevent the channel from restoring itself, the channel regains its ideal curvate alignment. Attempts to advance the cannula, once the channel has regained its curvate alignment, cause the sharp tip of the cannula to dig into the side wall of the channel. This is especially effective if the channel surface is ribbed, therein providing a substantial lip for the tip to dig into.

In a third embodiment, a similar cover element is provided, having an axial channel therethrough, but also including an interior chamber. A spring plate, having a forward engaging edge and pair of through holes therein, is mounted to the rear wall of the interior chamber. In an initial disposition, the forward engaging edge is forcibly held against the shaft of the cannula such that the through holes are aligned with the axial channel. The cannula is therefore provided a linear path along which to translate. After use, however, once the cannula is retracted through the axial channel, and backed into the interior chamber, the forward engaging edge of the spring is released. The expansion of the spring forward causes the through holes therein to become partially misaligned, therein gripping the shaft of the cannula. The cannula is thereby prevented from advancing by the grip of the holes in the spring plate as well as the forward engaging edge which is positioned in front of the axial channel, thus preventing the advance of the cannula.

DETAILED DESCRIPTION OF PREFERRED EMBODIMENT

Figure 1:
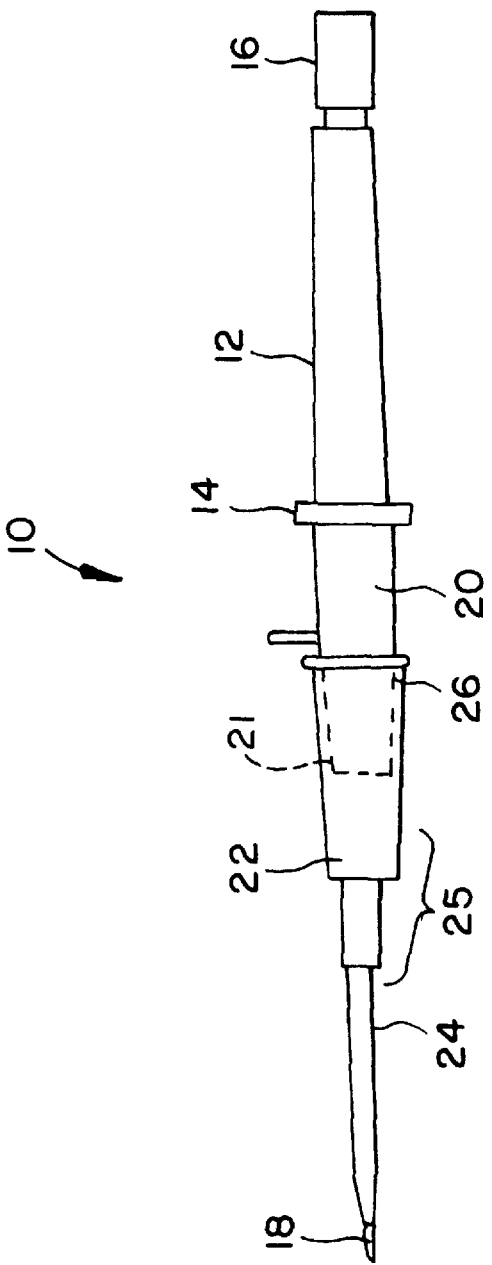
FIG. 1 is a side view of a medical assembly including a catheter, a cannula, a syringe, and the safety cover of the present invention.

This invention relates to the field of hypodermic needles and most particularly to devices for inserting catheters into blood vessels. Referring now to the drawings, FIG. 1 shows a catheter insertion apparatus 10 having a safety cover 20. The apparatus 10, which is shown in a side view, includes a syringe body 12, with an annular ring 14 at the base thereof, and a standard slidable plunger element 16 which translates within the syringe body 12. A cannula 18 extends axially outward from the annular ring 14; the narrow hollow internal passage within the cannula 18 providing a connection from the internal volume of the syringe body 12 to the exterior, through which fluids may flow.

The cannula 18 extends outward from the annular ring 14, through a safety cover 20. The safety cover 20, is constructed so that the cannula 18 may be inserted axially therethrough and so that the cannula 18 and the safety cover 20 may be translated relative to each other. In the embodiment shown in FIG. 1, the apparatus 10 further includes a catheter 25. The catheter 25 includes an elongate narrow, flexible, tube section 24, through which the cannula 18 is disposed prior to the catheter being inserted into the patient. The catheter 25 further includes a hub 22 having a widened receiving port 26, in which a portion of the safety cover 20 is initially nested. The nested portion 21 of the safety cover 20 is shown in phantom. The cannula 18 therefore extends outward from the annular ring 14 of the syringe body 12, sequentially through the safety cover 20, the widened receiving port 26 of the catheter hub 22, and ultimately through the elongate narrow flexible tube section 24.

In use the cannula 18 is disposed through the narrow flexible tube section 24, to enable puncturing and insertion of the flexible tube 24 through the skin of a patient, and positioning of the tube 24 into the desired blood vessel. If properly positioned in the blood vessel, the user withdraws the cannula 18 from the patient without removing the catheter element 22, therein providing an open conduit through which the medical care provider may draw blood, or input appropriate medication directly to the vasculature.

The process of removing cannulae from patients and decoupling syringes and cannulae from their corresponding catheter elements, in apparatus of the prior art, exposed the medical care providers to the sharp tip of the cannula which had been contaminated by the patient's blood. In the present invention, the receiving port 26 of the catheter hub 22 and the external surface of the safety cover 20 are releasably mated in the initial disposition of the apparatus 10. During extraction of the syringe 10 and cannula 18, the safety cover 20 and the receiving port 26 remain coupled until the tip of the cannula 18 is fully retracted into the safety cover 20. Once the tip of the cannula 18 is fully retracted, the safety cover 20 is released from the catheter hub 22. A variety of mechanisms for releasably holding the safety cover 20 to the receiving port 26 of the catheter hub 22 are shown in the art, any one of which may be employed in the present assembly. Such releasable couplings may be manually actuatable or automatically actuated by the retraction of the tip of the cannula 18.

Figure 2:
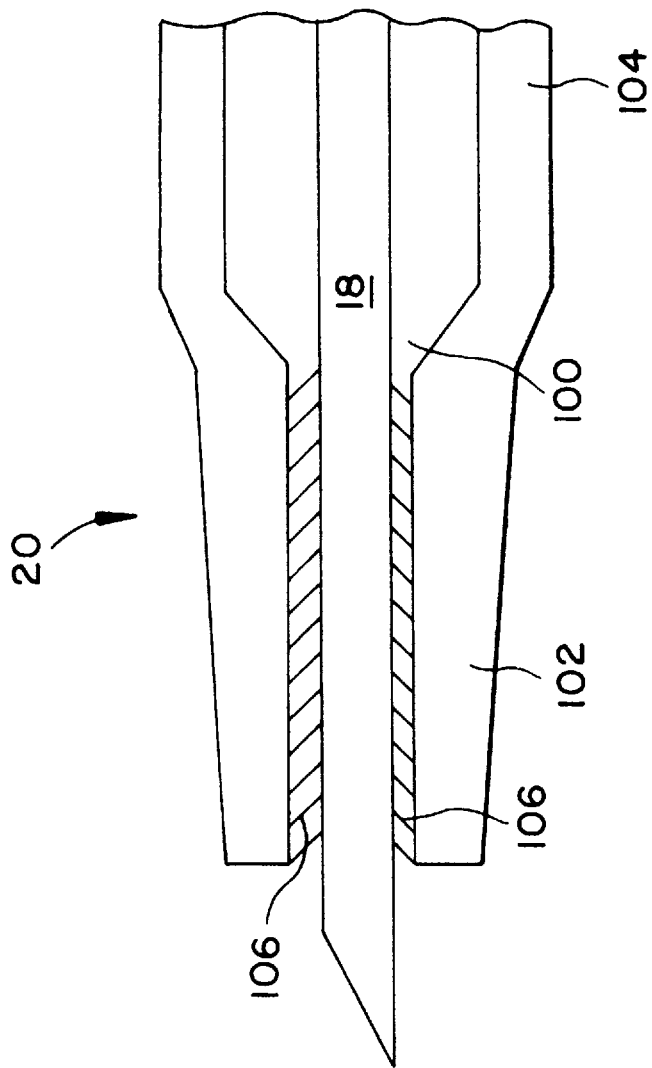
FIG. 2 is a side cross-section view of one aspect of the present invention including a plurality of reverse angle bristles, with the cannula in its initial position.

Referring now to FIG. 2, a side cross-section view of a first embodiment of the safety cover 20 of the present invention is provided wherein the cannula 18 and safety cover 20 are illustrated in their initial, pre-insertion, disposition in which the cannula 18 extends axially through the safety cover 20. More specifically, the cover comprises an elongate and generally cylindrical body having an axial channel 100, which extends from the forward portion 102, to a rearward portion 104. The portion of the axial channel 100 which extends through the forward portion 102 of the safety cover includes a plurality of flexible reverse angled bristles 106 which are angled and biased to allow movement of the tip inward to retract the tip into the cover, but to prevent reentry of the tip into the forward portion of the axial channel 100. The bristles 106 may comprise, for example plastic flashes or metal spikes. In the initial position, the cannula 18 causes the bristles 106 to be radially deflected radially as shown in FIG. 2 (the curved back sweep of the bristles 106).

Figure 3:
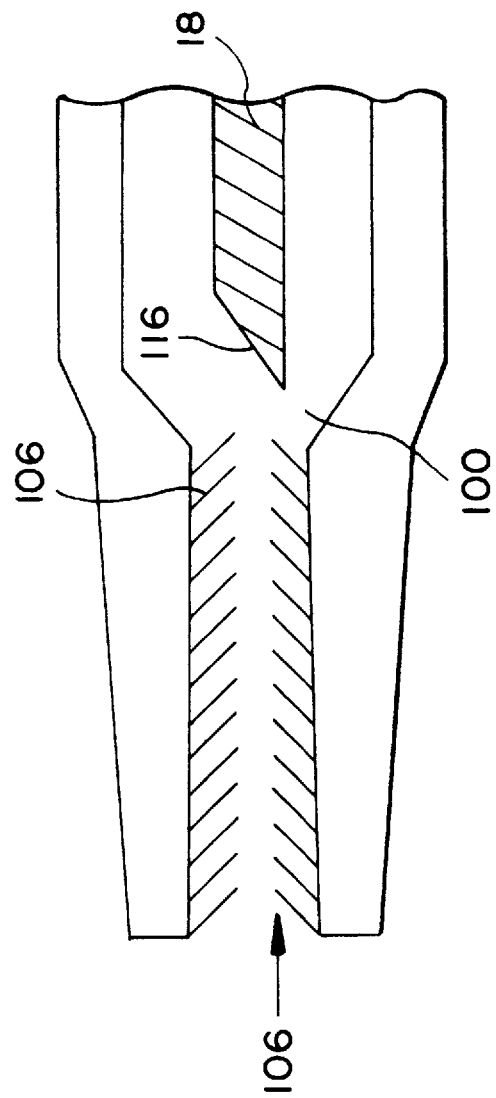
FIG. 3 is a side cross-section view of the aspect of the present invention shown in FIG. 2, wherein the cannula has been retracted and the reverse angle bristles prevent the advance of the cannula.

Referring now to FIG. 3, a side cross-section view of the apparatus shown in FIG. 2 is provided, wherein the tip of the cannula 18 has been retracted. As is shown, the retraction of the tip 116 of the cannula 18 beyond the forward portion of the axial channel 100 necessarily frees the bristles 106 from the compressive influence of the cannula 18. Once freed from the axial alignment provided by the shaft of the cannula 18, the bristles 106 spring back into position and effectively block the forward translation of the cannula through that portion of the channel 100.

Figure 4:
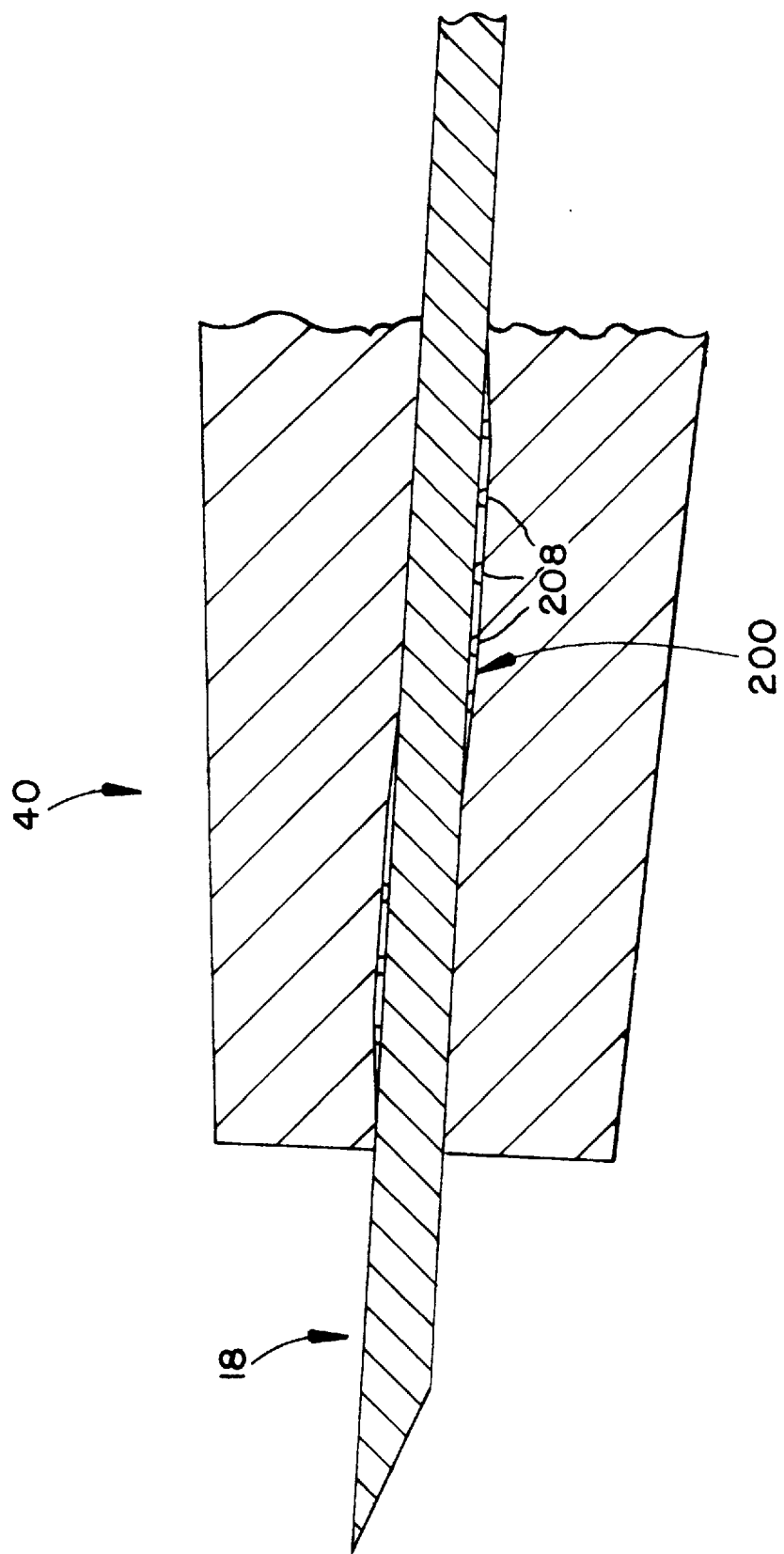
FIG. 4 is a side cross-section view of another aspect of the present invention including a ribbed curvate axial channel, with the cannula in its initial position.
Figure 5:
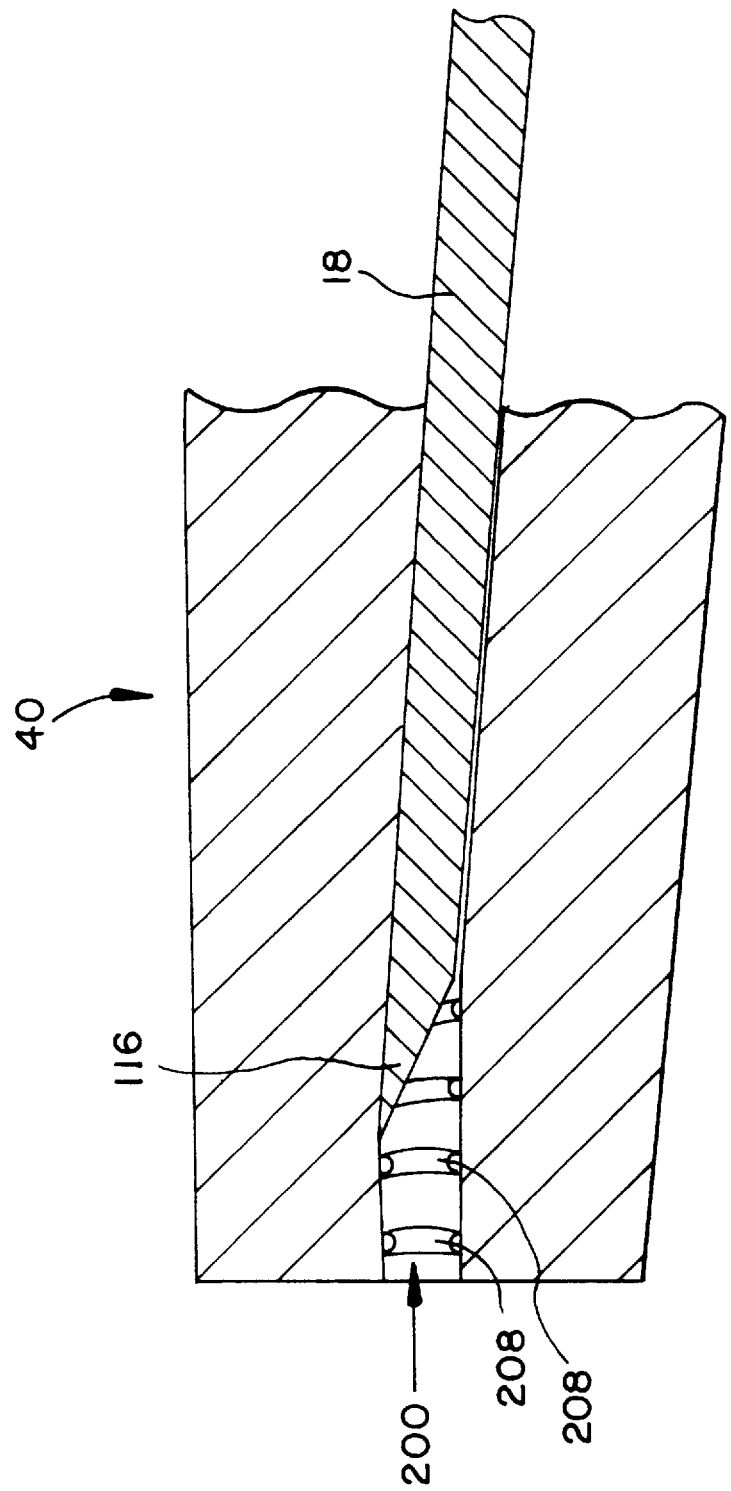
FIG. 5 in a side cross-section view of the aspect of the present invention shown in FIG. 4, wherein the cannula has been retracted and subsequently partially advanced into the ribbed curvate channel.

Referring now to FIGS. 4 and 5, a second embodiment of the present invention is provided in cross-section views showing the cannula 18 and the safety cover 40 in the initial and retracted positions, respectively. More particularly with respect to FIG. 4, the axial channel 200 is formed of a resilient and semi-flexible material, for example a moldable thermoplastic, having a slight curvature, and the interior surface comprising a plurality of ribbings 208. In this initial position, the cannula extends fully through the slightly curved axial channel, thereby imparting a straightening force to the channel 200.

Referring, in particular, to FIG. 5, the disposition of the cannula 18 with respect to the axial channel 200 is shown wherein the tip 116 of the cannula has been retracted into the channel, and subsequently forced forward. Once the cannula 18 is retracted into the cover 40, the shaft thereof no longer provides a straightening influence to the axial channel 200. Without the straightening influence, the resilient and semi-flexible character of the cover material permits the channel 200 to regain its original slightly curvate shape. Inasmuch as the cannula 18 includes a sharp tip 116, and is not constructed of a similarly semi-flexible material (cannulae are generally constructed of surgical steel or other suitably rigid metal), attempted reinsertion of the cannula 18 through the axial channel 200 causes the tip 116 to dig into the side wall surface thereof. The ribbings 208 of the side wall surface of the axial channel 200 provide particularly ideal sites for the tip 116 to catch and dig.

It is understood that the number of ribbings 208 or bristles 106 utilized is an engineering expedient which does not alter the teachings of the present invention in any way. It is entirely anticipated that one may chose to include ribbings or bristles of any suitable length, depth, shape, size, or depth which are sufficient to prevent reinsertion of the cannula 18.

Figure 6:
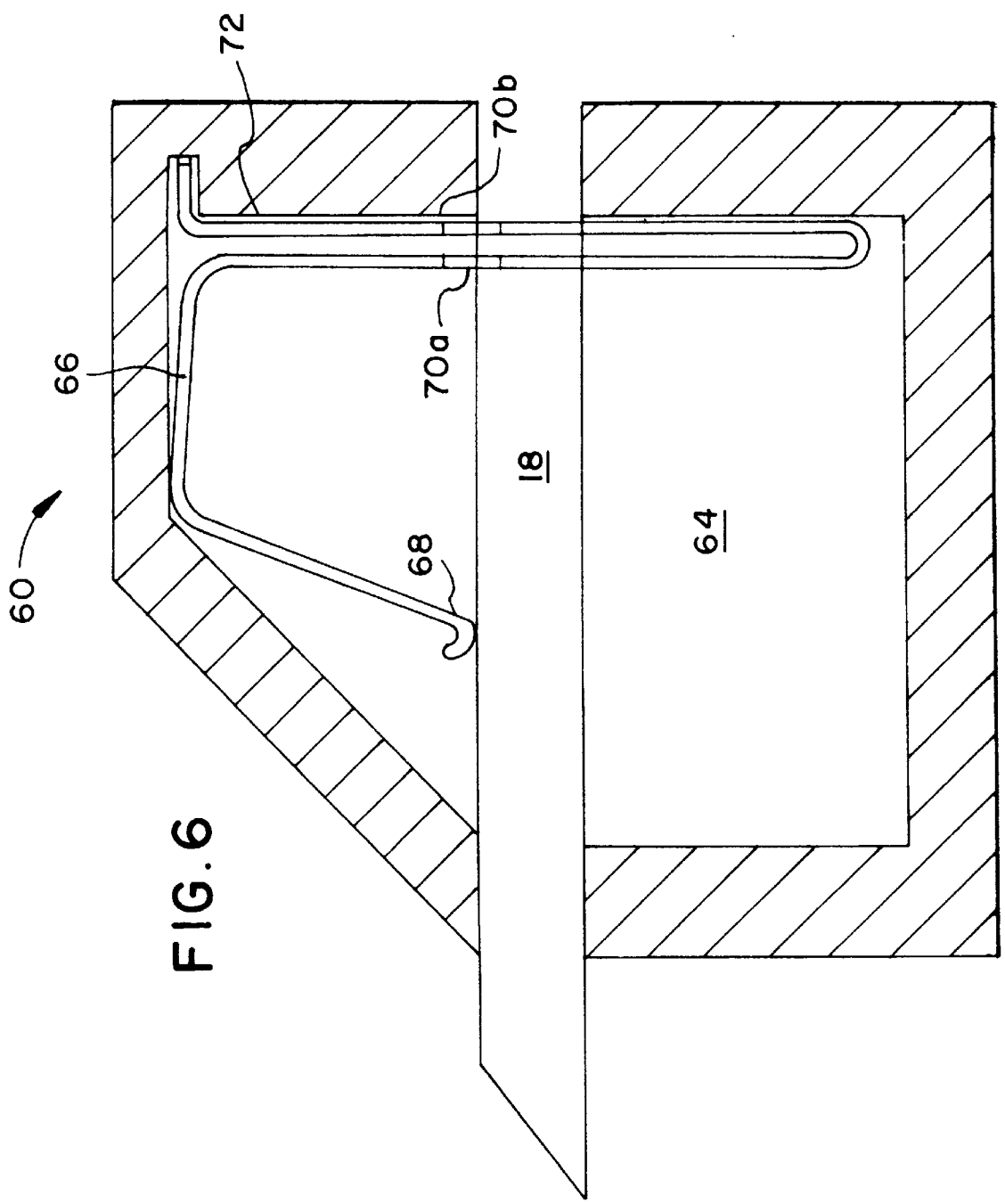
FIG. 6 is a side cross-section view of an aspect of the present invention including a spring plate, disposed in its initial compressed position with the cannula positioned therethrough.
Figure 7:
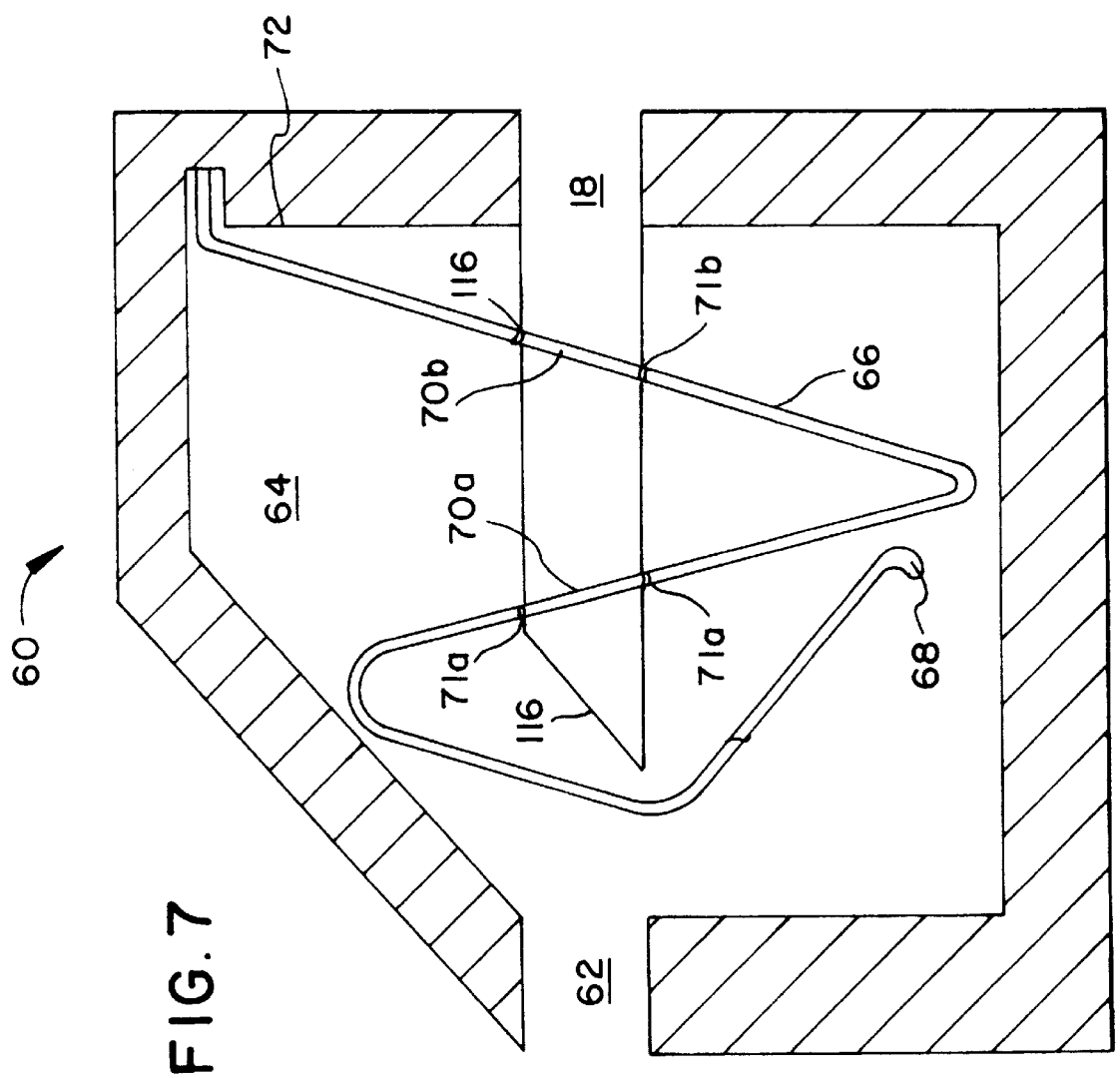
FIG. 7 is a side cross-section view of the aspect of the present invention shown in FIG. 6, wherein the cannula has been retracted and spring plate has advanced, thereby preventing the cannula from advancing.

Referring now to FIGS. 6 and 7, a side cross-section view of a third embodiment of the present invention is provided, wherein the safety cover 60 is shown having the cannula 18 in its initial, fully inserted position through the axial channel 62. With respect to FIG. 6, a cover element 60 is provided, having a linear axial channel 62 therethrough which includes an interior chamber 64. A spring plate 66, having a forward engaging edge 68 and pair of through holes 70a,70b therein, is mounted to the rear wall 72 of the interior chamber 64. In an initial disposition, the spring 66 is compressed by virtue of the fact that the forward engaging edge 68 is forced upward to rest against the shaft of the cannula 18. The through holes 70a,70b of the spring plate 66 are aligned under the compression described above. The cannula 18 is therefore provided a linear path along which to translate.

Referring now to FIG. 7, after the cannula 18 has been used, it is retracted through the axial channel, and the tip 116 is drawn back beyond the forward engaging edge 68 of the spring 66. Once the positioning influence of the cannula 18 is removed, the edge 68 and spring 66, are permitted to advance downward and forward. The expansion of the spring 66 causes the through holes to move relative to the axial channel 62 of the safety cover, therein becoming partially misaligned. In this partially misaligned position, the rims 71a,71b of the through holes 70a,70b, respectively, grip the shaft of the cannula 18, locking the cannula in position. In addition, the forward edge 68 moves into a blocking position in front of the forward portion of the axial channel 62 of the safety cover. The cannula 18 is thereby prevented from advancing by the grip of the holes 70a,70b in the spring plate 66 as well as the forward engaging edge 68 which is positioned in front of the axial channel 62, thus preventing the advance of the cannula.

While there has been described and illustrated specific safety covers for preventing accidental "needle sticks" with contaminated needles, it will be apparent to those skilled in the art that variations and modifications are possible without deviating from the broad spirit and principle of the present invention which shall be limited solely by the scope of the claims appended hereto.

What is claimed is:

1. A safety cover and cannula assembly for locking a tip of said cannula therein, comprising:

an elongate body having an interior chamber, said elongate body being slidably mountable on said cannula;

an axial channel, extending along the entire axial length of the elongate body, from a forward portion of the body, to a rearward portion, said axial channel slidably receiving therethrough the cannula; and means disposed in said axial channel which displaces upon retraction of the tip of said cannula, whereby subsequent advancement of said cannula fully through said safety cover is prevented wherein said means comprises a plurality of bristles which are angled and biased to allow movement of the tip inward to retract into the cover, but which bristles prevent reentry of the tip into the forward portion.

2. The safety cover assembly set forth in claim 1, wherein said bristles comprise plastic flashes.

3. The safety cover assembly set forth in claim 1, wherein said bristles comprise metal spikes.

4. A safety cover and cannula assembly for locking a tip of said cannula therein, comprising:

an elongate body having an interior chamber, said elongate body being slidably mountable on said cannula;

an axial channel, extending along the entire axial length of the elongate body, from a forward portion of the body, to a rearward portion, said axial channel slidably receiving therethrough the cannula;

means disposed in said axial channel which displaces upon retraction of the tip of said cannula, whereby subsequent advancement of said cannula fully through said safety cover is prevented; and wherein said forward portion of said elongate body comprises a resilient semi-flexible quasi-elastomeric material having a curvate bias, whereby the axial channel bends due to the quasi-elastomeric material properties upon retraction of said cannula such that forward motion of the cannula relative to the forward portion after retraction causes the tip to dig into the forward portion, thereby preventing tip advancement therethrough.

5. The safety cover assembly set forth in claim 4, wherein said axial channel further comprises a plurality of radial ribs.

* * * * *